(12) United States Patent
Chase et al.

(10) Patent No.: US 11,135,368 B2
(45) Date of Patent: Oct. 5, 2021

(54) ESTIMATION OF FUTURE INSULIN SENSITIVITY DISTRIBUTIONS

(71) Applicant: TIRO Medical Limited, Christchurch (NZ)

(72) Inventors: James Geoffrey Chase, Christchurch (NZ); Jennifer Launa Knopp, Christchurch (NZ); Christopher Grant Pretty, Christchurch (NZ); Vincent Uyttendaele, Christchurch (NZ)

(73) Assignee: TIRO Medical Limited, Christchurch (NZ)

( * ) Notice: Subject to any disclaimer, the term of this patent is extended or adjusted under 35 U.S.C. 154(b) by 294 days.

(21) Appl. No.: 16/385,103

(22) Filed: Apr. 16, 2019

(65) Prior Publication Data
US 2019/0328966 A1    Oct. 31, 2019

Related U.S. Application Data

(60) Provisional application No. 62/662,992, filed on Apr. 26, 2018.

(51) Int. Cl.
| | |
|---|---|
| *A61M 5/172* | (2006.01) |
| *A61B 5/145* | (2006.01) |
| *A61B 5/00* | (2006.01) |
| *G16H 50/20* | (2018.01) |
| *G16H 20/17* | (2018.01) |

(52) U.S. Cl.
CPC ....... *A61M 5/1723* (2013.01); *A61B 5/14532* (2013.01); *A61B 5/4839* (2013.01); *A61B 5/7275* (2013.01); *G16H 20/17* (2018.01); *G16H 50/20* (2018.01); *A61M 2205/50* (2013.01); *A61M 2205/502* (2013.01); *A61M 2205/52* (2013.01); *A61M 2230/201* (2013.01)

(58) Field of Classification Search
CPC ............ A61M 5/1723; A61B 5/14532; A61B 5/7275; A61B 5/4839; G16H 20/17; G16H 50/20; G16H 50/30; G16H 20/10
See application file for complete search history.

(56) References Cited

U.S. PATENT DOCUMENTS 8,005,524 B2 * 8/2011 Brauker .............. A61M 5/1723
600/345

\* cited by examiner

*Primary Examiner* — Manuel A Mendez
(74) *Attorney, Agent, or Firm* — Bond Schoeneck & King, PLLC; Joseph Noto

(57) ABSTRACT

A method and device for using insulin sensitivity values to estimate the distribution of future insulin sensitivity values for a given patient based on dimensional relationships between current, prior and delta insulin sensitivity values, and observed future insulin sensitivity values for similar patients or subjects, or based on an individual patient or subject's historical values.

12 Claims, 8 Drawing Sheets

ESTIMATION OF FUTURE INSULIN SENSITIVITY DISTRIBUTIONS

CROSS REFERENCE

This application claims the benefit of the filing date of U.S. Provisional Patent Application Ser. No. 62/662,992, filed Apr. 26, 2018, which is hereby incorporated by reference in its entirety.

FIELD

The present invention relates to a glycaemic control device and methods for insulin sensitivity prediction and control.

BACKGROUND

Insulin sensitivity (SI) is a main determinant of blood glucose level in all humans and animals with metabolism. In diabetes, insulin resistance and hyperglycemic hospital patients, deranged blood glucose levels are treated with insulin and/or nutrition and/or activity. Activity affects SI levels and need for nutrition, and insulin and nutrition act in balance to yield outcome glycemia. Controlling blood glucose levels can be very difficult as SI can vary substantially, particularly in hospitalized patients.

Insulin therapy for glycaemic control (GC) in critically ill patients improves outcomes by reducing hyperglycaemia and glycaemic variability, which are both associated with increased morbidity and mortality. However, results have proven difficult to repeat or achieve safely.

Critically ill patients in intensive care units (ICUs) often experience abnormally elevated blood glucose concentrations (hyperglycaemia), as a stress response to illness and injury. Hyperglycaemia, glycaemic variability, and hypoglycaemia are all independently associated with increased morbidity and mortality. Glycaemic control using insulin therapy has shown beneficial outcomes, reducing organ failure and costs but with increased risk of hypoglycaemia with tight control.

GC has been hard to achieve both safely and effectively. Fixed or ad hoc protocols are still typically used in hospitals, but fail to capture and fully account for patient variability impacting performance and safety. This issue has led to the emergence of more complex, model-based GC protocols.

STAR (Stochastic TARgeted) is a clinically-validated model-based GC framework, capable of adapting treatment to patient-specific insulin requirements while managing the risk of hypoglycaemia.

The stochastic model currently used by STAR forecasts future SI (SIn+1) distributions based on the identified current SI value (SIn). A Markov process is used, where outcome SIn+1 only depends on input SIn. This allows risk based rather than target based dosing. However, STAR has been found to be overly conservative and there is a need for an approach using more data inputs with a noncomplex model to more rapidly bring insulin/glucose levels into a stable, safe level.

Thus, more optimal treatment could be provided if there was a means to predict future distributions of SI as likelihoods. From these distributions, explicit quantifiable risks could be created to assess an individual's health state and/or adjust treatment. These predictions could be patient-specific or more generally related to a cohort or similar or otherwise grouped individuals.

SUMMARY

In accordance with one aspect of the present invention, there is provided a method for controlling the blood glucose levels of a patient including the steps of:
a) measuring the blood glucose level of the patient;
b) determining the current insulin sensitivity of the patient;
c) estimating with a multi-dimensional model the adjustment needed to obtain a blood glucose level between a desired lower and upper confidence interval after administration of the estimated adjustment to the patient;
d) administering the estimated adjustment to the patient; and
e) repeating steps a) through d) until a desired state of health is achieved.

In accordance with another aspect of the present disclosure, there is provided a device for controlling the blood glucose levels of a patient, including:
a processor programmed to forecast with a multi-dimensional model based on the current insulin sensitivity and the % change in insulin sensitivity from a prior insulin sensitivity value, the adjustment needed to obtain a blood glucose level between a desired lower and upper confidence interval after administration of the estimated adjustment to the patient;
a memory;
a data input; and
a display.

In accordance with another aspect of the present disclosure, there is provided a device for controlling the blood glucose levels of a patient, including: a processor programmed to forecast with a multi-dimensional model based on the current SI and the % change in SI from a prior SI value, the insulin/nutritional adjustment needed to obtain a blood glucose level between upper and lower CIs (e.g., the 5% and 95% CI) after administration of the forecasted insulin/nutritional adjustment to a patient; a memory; a data input; and a display.

These and other aspects of the present disclosure will become apparent upon a review of the following detailed description and the claims appended thereto.

DETAILED DESCRIPTION

Figure 1:
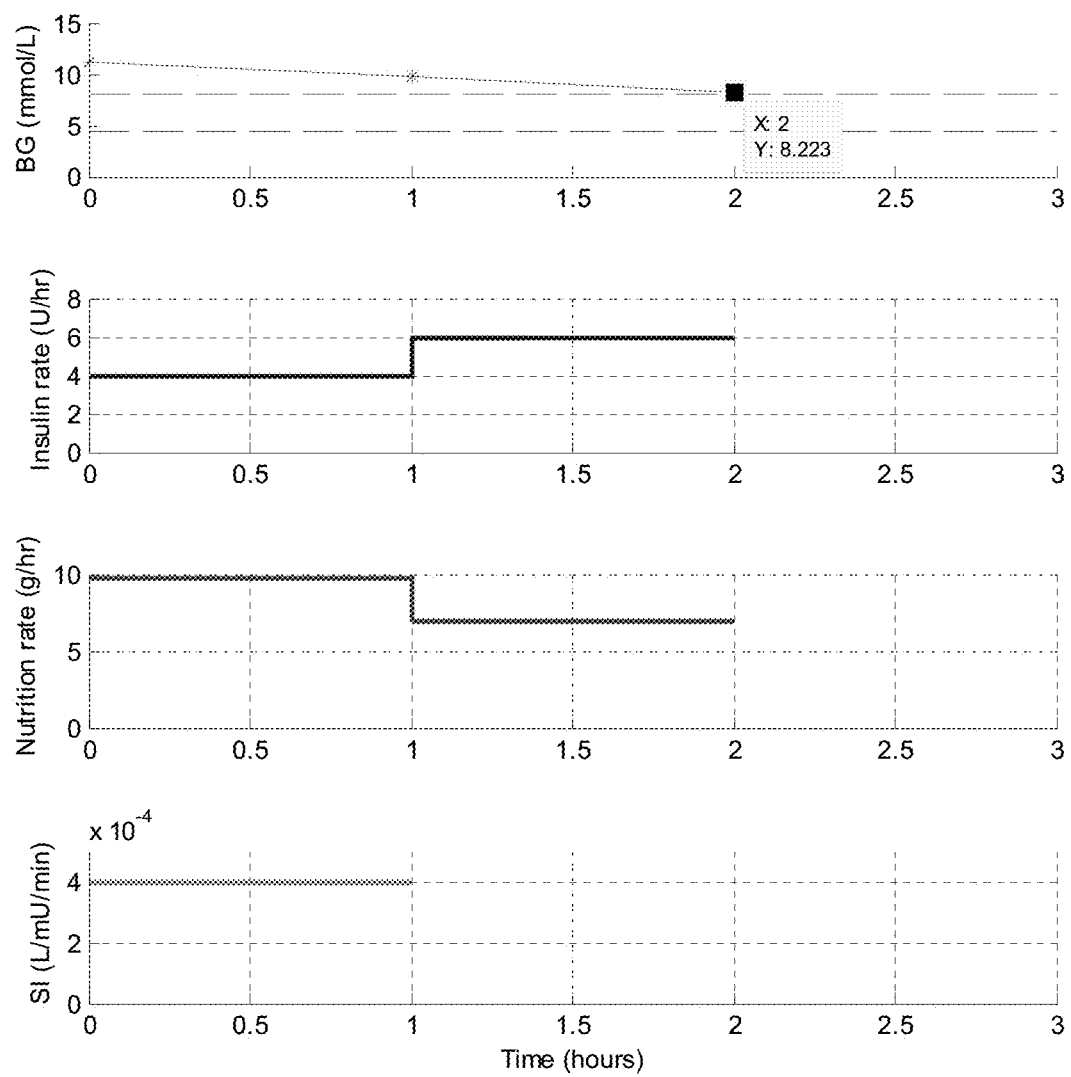
FIG. 1 shows the input values to calculate SI(t=2) in accordance with the Example of the present invention.

A method for controlling the blood glucose level of a patient includes the steps of:

a) measuring a blood glucose level and determining an insulin sensitivity of the patient;

b) measuring, subsequent to step a), the blood glucose level and determining the current insulin sensitivity of the patient;

c) estimating with a multi-dimensional model, comprising delta SI, the adjustment needed to obtain a blood glucose level between a desired lower and upper confidence interval after administration of the estimated adjustment to the patient;

d) administering the estimated adjustment to the patient; and e) repeating steps b) through d) until a desired state of health is achieved.

The multi-dimensional data base can be constructed according to the following procedure. Accumulation of relevant physiological data used or used to derive patient specific physiological metrics (e.g., SI from glucose, insulin, nutrition data; or pulse pressure variation from arterial pressure waveforms; or HRV heart rate variability from heart rate ECG data) calculated from data directly or via a model from a plurality of patients. This data can be stored for each patient over time and can then be processed or organized in N-dimensional groups based on what sets of inputs and resulting output(s) are desired.

Using measured data from a large multinational cohort, SI values may be obtained from a model, such as auto regressive or neural network. The model includes the relationships of current SI, delta SI, and the adjustment level to future SI. For any individual, a history or trajectory of SI values can be collected prospectively or retrospectively. These trajectories of values can be used to create relationships between current or recent SI(n), its changes and other relevant input values to predict a future SI(n+dt), for example, where dt=30 minutes to 48 hours or more.

In an embodiment, the multi-dimensional model is based upon clinical input data. Suitable input includes the following: physiological measurements; severity of health condition scores based on measurements and/or diagnoses and/or treatments; or anthropomorphic metrics, including sex, size, weight, height, and the like; or any metric derived from one or more thereof. Suitable input also includes the following: current SI and prior SI or % delta SI; current and prior blood glucose levels; current and prior HR, HRV or other metrics accounting for activity or exercise; current diagnosis (in hospital) or severity score (Apache II, SAPS, TISS, SOFA or similar diagnostic or severity score); predicted future interventions of insulin and/or nutrition and/or exercise or other metrics accounting for activity or exercise; or any metric derived from one or more thereof. These inputs allow more personalized predictions of glucose levels and more aggressive treatment with insulin and/or nutrition without safety issues. The clinical input data can be derived from an individual or group or sub-cohort of individuals, including male groups, or female groups.

According to an embodiment, all possible sets of input data are contemplated. These sets are grouped into a set of vertices in that n-space, the number is known as well as the total number of possible input data sets within the database. Equally with kernel density, this grouping is done mathematically using a statistical distribution. Thus, the likelihood of any input data set is calculated from the nearby sets of input parameters that are similar. From this calculation, the likelihood of occurrence can be calculated.

According to an embodiment of a method to assess or alarm for potential input errors in SI, the clinical data used to evaluate SI, and/or other input data when an input has (clinically or otherwise selected) very low probability of occurrence (below any set threshold) and thus lies in a region of low or no existing data. Such errors arise from a range of either data input errors or failures in care, including errors in clinical data, data input errors, failed pump, false measurement, or failure to eat a meal, glucose or any other sensor error or any other incorrect input due to error or misuse.

Figure 3:
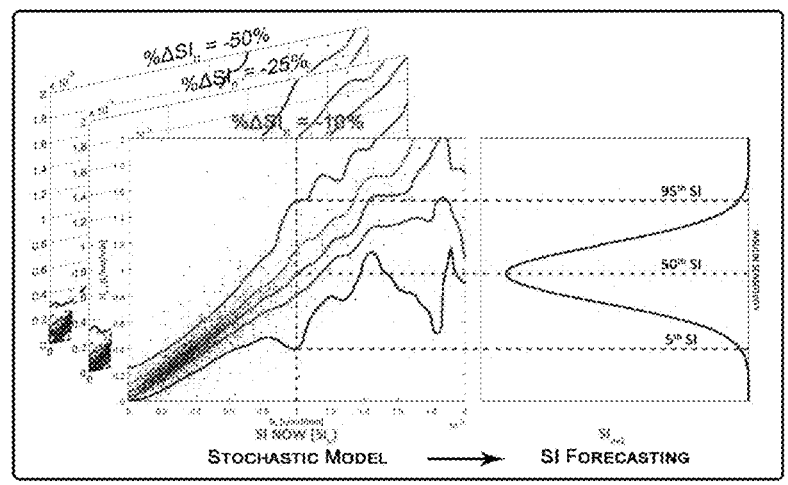
FIG. 3 shows the forecasted SI at a future time at different % delta SI values using stochastic model in accordance with an embodiment of the present invention.
Figure 4:
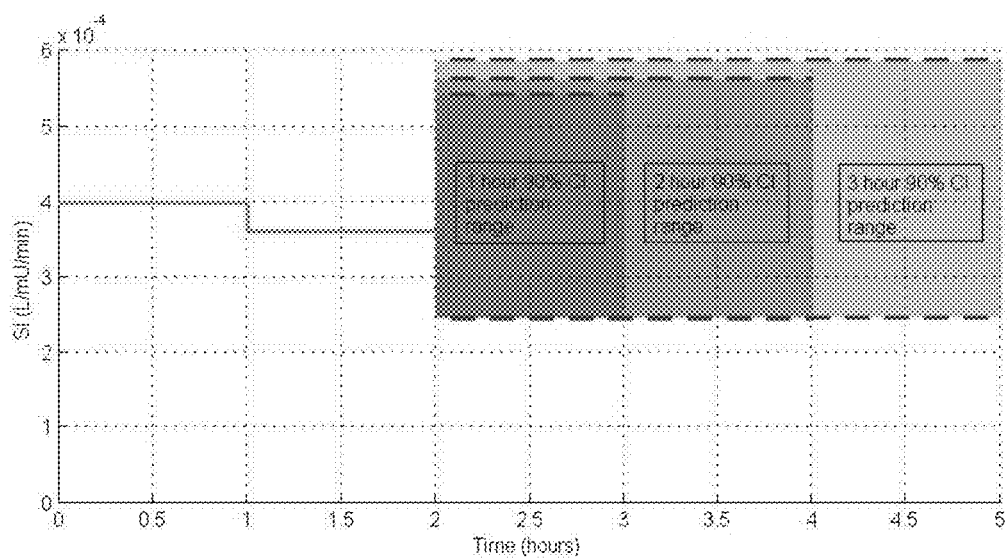
FIG. 4 shows the forecasted bands (90% CI) of SI at various future times in accordance with an embodiment of the present invention.

According to an embodiment, as an example, the model at any given point could be adjusted to within a specified range, e.g., a target of 4.5 mmole/L. The target can be set as 10 to 90% or 5 to 95% probability and also a lower limit of the next point to be below 3. The model shows the risk for a certain amount of insulin and nutrition. An example can be seen in FIG. 3 where the prediction shows what could happen with various insulin and nutrition inputs.

Certain identified levels of blood glucose can correspond to what is light, mild, moderate or severe hypoglycemia. The model would then give results of what is the risk of landing in the mild to severe range. In general a clinician would pick input that is predicted to avoid hypoglycemia. In practical use in ICU this model has reduced hypoglycemia to a very low level compared to ICU not using the model.

A primary and exemplar embodiment relates to a multi-dimensional model developed on the ability to predict more accurate future SI distributions, using both current SI and its percentage change from the prior value. In an embodiment, SI is obtained from 70,000 hours of clinical data to create a multi-dimensional stochastic model.

An embodiment of a multi-dimensional model characterises patient specific metabolic variability and patient specific response to insulin, allowing more optimal insulin dosing to increase performance and safety. This method expands the prior 2D stochastic approach by adding the most recent change in $SI_n$ as an input parameter for forward prediction of outcome $SI_{n+1}$. The multi-dimensional model of the present invention predicts future $SI_{n+1}$ based on current $SI_n$ and the percentage change in SI from $SI_{n-1}$ to $SI_n$.

The ICING (Intensive Control Insulin-Nutrition-Glucose) physiological model describing glucose-insulin dynamics is defined as:

$$\dot{G} = -p_G \cdot G(t) - SI \cdot G(t) \frac{Q(t)}{1 + \alpha_G \cdot Q(t)} + \frac{P(t) + EGP - CNS}{V_G} \quad (1)$$

$$\dot{I} = n_K \cdot I(t) - n_L \frac{I(t)}{1 + \alpha_I \cdot I(t)} - n_I(I(t) - Q(t)) + \frac{u_{ex}(t)}{V_I} + (1 - x_L) \frac{u_{en}(G)}{V_I} \quad (2)$$

$$\dot{Q} = n_I(I(t) - Q(t)) - n_C \frac{Q(t)}{1 + \alpha_G Q(t)} \quad (3)$$

Where G(t) is the blood glucose level (mmol/L), I(t) is the plasma insulin concentration (mU/L), Q(t) is the interstitial insulin concentration (mU/L), P(t) is the glucose appearance in plasma from enteral and parenteral dextrose intake (mmol/min), and SI is insulin sensitivity (L/mU/min).

Model-based insulin sensitivity (SI) is patient-specific and time varying, characterizing patient-specific glycaemic system response to glucose and insulin administration. SI is identified hourly from clinical BG, and insulin and nutrition input data, using an integral-based fitting method.

The model-based glycaemic controller is a clinically validated model which identifies current patient-specific insulin sensitivity using metabolic data, and forecasts likely blood glucose (BG) outcomes for a given insulin and nutritional adjustment by assessing inter- and intra-patient variability. However, the model's predictions and the patient outcome may differ, and the difference is a random variable. This is not surprising, as the typical use of the data is to administer insulin and nutrition so as to affect the expected result, so it is likely that the actual result will stray from the expected value. Clearly to have an expected result there needs to be evidence, in terms of past clinical results, to base the expected effects. The variability is and has been captured as a multi-dimensional probability distribution gathered from a large population of patient data. The distribution of past data can be applied as a stochastic model of affects from the administration of insulin and nutrition. The distribution of past data can be used to determine the expected result, but additionally, the distribution of results from an administration of insulin and nutrition are established. Using the distribution it is possible to predict the range of likely future variation of SI over the following hours (e.g., 1 to 3) after an insulin and nutritional adjustment. This can be used to positively affect patient safety, as adverse responses can be greatly reduced.

In the following the SI levels are indexed based upon the administration of insulin and nutrition. SI is determined by solving a differential equation that utilizes parameters obtained from clinical data. One standard method of solving the differential equation is the so-called integral based method, a forward differencing scheme, though other approaches are available. Hence $SI_0$ is the initial insulin sensitivity value and $SI_n$ is the $n^{th}$ administration. Inputs to the methods utilize the current value ($SI_n$) and its percentage change from prior intervention (%$\Delta SI_n$). This range is used to compute the optimal insulin and nutritional adjustment resulting in BG outcomes that best overlap a targeted band (e.g., 4.4 to 6.6 mmol/L) while minimizing risks of hypoglycaemic events, ensuring a maximum 5% risk of predicted BG outcomes below a lower limit (e.g., 4.4 mmol/L). An administration where the overlap is at least 90% is considered clinically safe.

An embodiment of a step-by-step approach is detailed below: A current model-based $SI_n$ parameter is identified for the patient using available clinical data (e.g., insulin rates, nutrition rates, and current blood glucose level ($BG_n$)). Optionally, determine the prior percentage change in SI in accordance with the formula $$\% \Delta SI_n = 100 \times \frac{SI_n - SI_{n-1}}{SI_{n-1}},$$

when the prior SI parameter, $SI_{n-1}$, is available. It is understood that the change can be ascertained once an administration has occurred and clinical measurements have been attained.

Calculate, utilizing the stochastic model, the 90% CI of likely variation of SI, represented as ($SI_{n+i}$), over each of the next 1, 2, and 3 hours based on $SI_n$ and % $\Delta SI_n$. A consideration is given to the fact that a patient's response to an insulin administration might cause the BG to become too high or too low and put a patient into a high risk situation. An insulin administration where this event is less than 10% likely is considered as safe. This is done by taking marginal distributions where the insulin administration is held constant and identifying where to overlap of the distribution and the region of safe BG levels are attained. Integrating the distribution in the safe region provides a confidence level of patient safety for a given dose. Finding a dose which meets these considerations is a solution to balancing the moving the patient to a desired BG level and maintaining a confidence the patient will not encounter undesirable affects.

The disclosure will be further illustrated with reference to the following specific examples. It is understood that these examples are given by way of illustration and are not meant to limit the disclosure or the claims to follow.

Example—Case Study

A patient has been under STAR for a couple hours because of hyperglycaemia.

Nutrition, insulin, previous BG levels and previous identified SI levels have been recorded and are thus known. It is now 2 hours after the beginning of STAR (t=2), and it is time to calculate the new treatment.

Step 1 (SI Identification):

A new measure of BG is taken: BG(t=2)=8.223 mmol/L.

Nutrition rate (6.7 g/hr) and insulin rate (6 U/hr) over the last period are known.

Only current SI is unknown at this point but can be determined using integral based methods as it is the only unknown parameter.

Solving the system of equations from the physiological model for SI over the last hour as shown in FIG. 1 gives:

$SI(t=2)=3.5951e-4$ L/mU/min.

Figure 2:
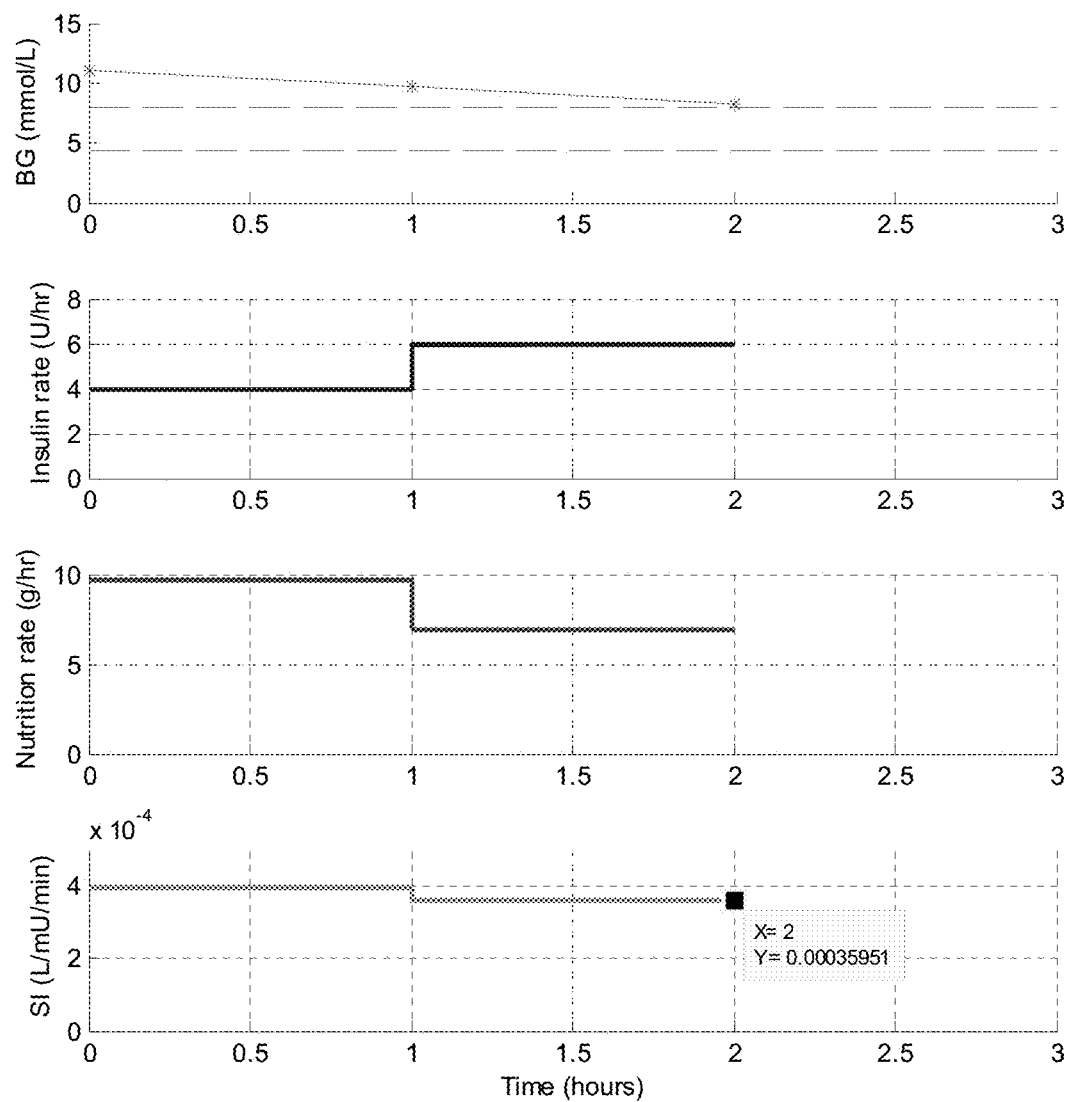
FIG. 2 shows the calculation of SI(t=2) using the physiological model in accordance with an embodiment of the present invention.

Step 2 (SI Previous Variability):

This new SI value (see FIG. 2) already gives an idea of the previous patient-specific metabolic variability (over the last two hours). Another metric can be used to describe this variability:

$$\% \Delta SI_n = 100 \times \frac{SI_n - SI_{n-1}}{SI_{n-1}}$$

It represents the hour-to-hour percentage SI variability (the % change from the previous to current SI value).

$SI(t=1)=3.9745e-4$ $SI(t=2)=3.5951e-4$

%$\Delta SI(t=2)=-9.55\%$

SI decreased of 9.55% from its previous value (the patient is quite stable, but slightly more resistant to insulin than the previous hour).

Step 3 (Identification Future SI Variability):

Now STAR knows the past/current patient-specific state, it will determine how likely it will change in the future. Thus, it will use the stochastic model (constructed on population data) with the identified current SI and % $\Delta$SI as inputs, to predict the 90% CI range of likely future SI(t=3) value. In other words, a range within which we are confident at 90% that the future SI(t=3) will fall in, based on the previous patient-specific SI evolution.

Given % $\Delta$SI(t=2)=-9.55% and SI(t=2)=3.5951e-4, the resulting 90% CI range for predicted SI(t=3) is:

[2.4390e-4,5.4042e-4]

This step can also be done to predict likely future SI in 2 or 3 hours:

90% CI range for $SI(t=4)$: $[2.4380e-4, 5.6128e-4]$

90% CI range for $SI(t=5)$: $[2.4548e-4, 5.8596e-4]$

Generally wider bands represent longer prediction times (more likely to have higher variability over longer periods of time).

Step 4 (Treatment Computation):

Based on this assessment of likely evolution of patient variability (future SI variability/evolution), STAR will use the physiological/mathematical model again, but slightly differently.

This time, knowing SI range (SI is not unknown anymore), we want to determine what intervention (insulin and nutrition) to give to the patient so the resulting predicted BG range (because this is based on predicted values of SI) is within the clinically specified safe target range. Thus:

SI is known ($5^{th}$ and $95^{th}$ percentiles of future SI)

Nutrition and Insulin rates are now variables

BG is now the only unknown of the equations, which can be determined solving the sets of equations.

Note: There exists a discrete number of insulin/nutrition combination due to clinical settings constraints (i.e., Insulin rate can range from 0 to 9 U/hr with 0.5 U/hr increment steps with maximum 2 U/hr increment, nutrition can vary from 30 to 100% of the total original goal feed with 5% increment steps and maximum of 30% change).

STAR will thus loop through all the possible insulin/nutrition combinations and find the optimal solution: adjusting the $5^{th}$ percentile of predicted BG to 4.4 mmol/L while maximizing overlapping with the target band. This ensures a maximum risk of 5% of hypoglycaemia. STAR always aim to maximize nutrition.

Figure 5:
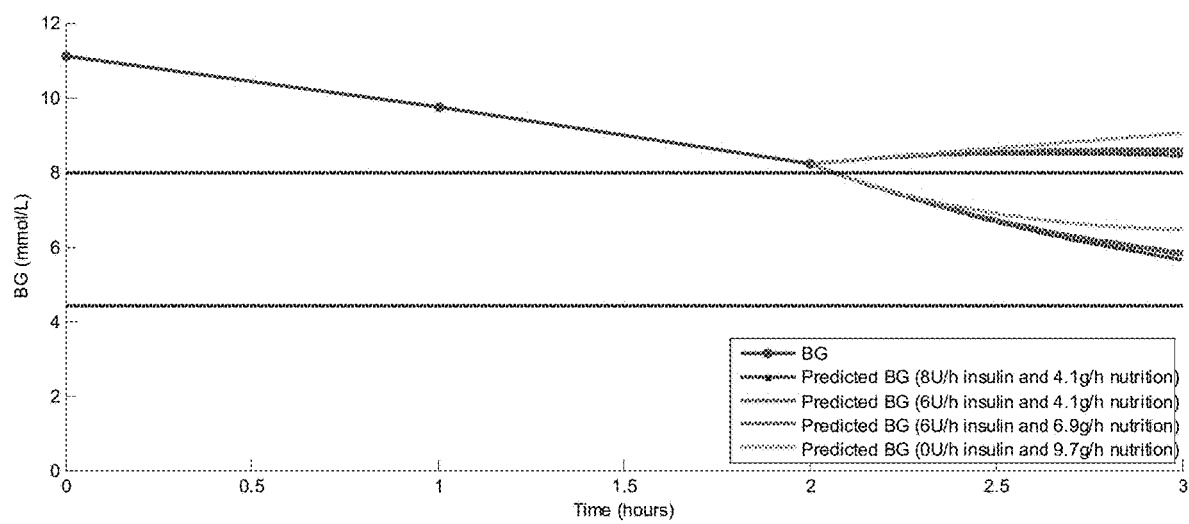
FIG. 5 shows the prediction of BG traces ($5^{th}$ and $95^{th}$ percentile) for different combination of insulin and nutrition inputs in accordance with the Example of the present invention.
Figure 6:
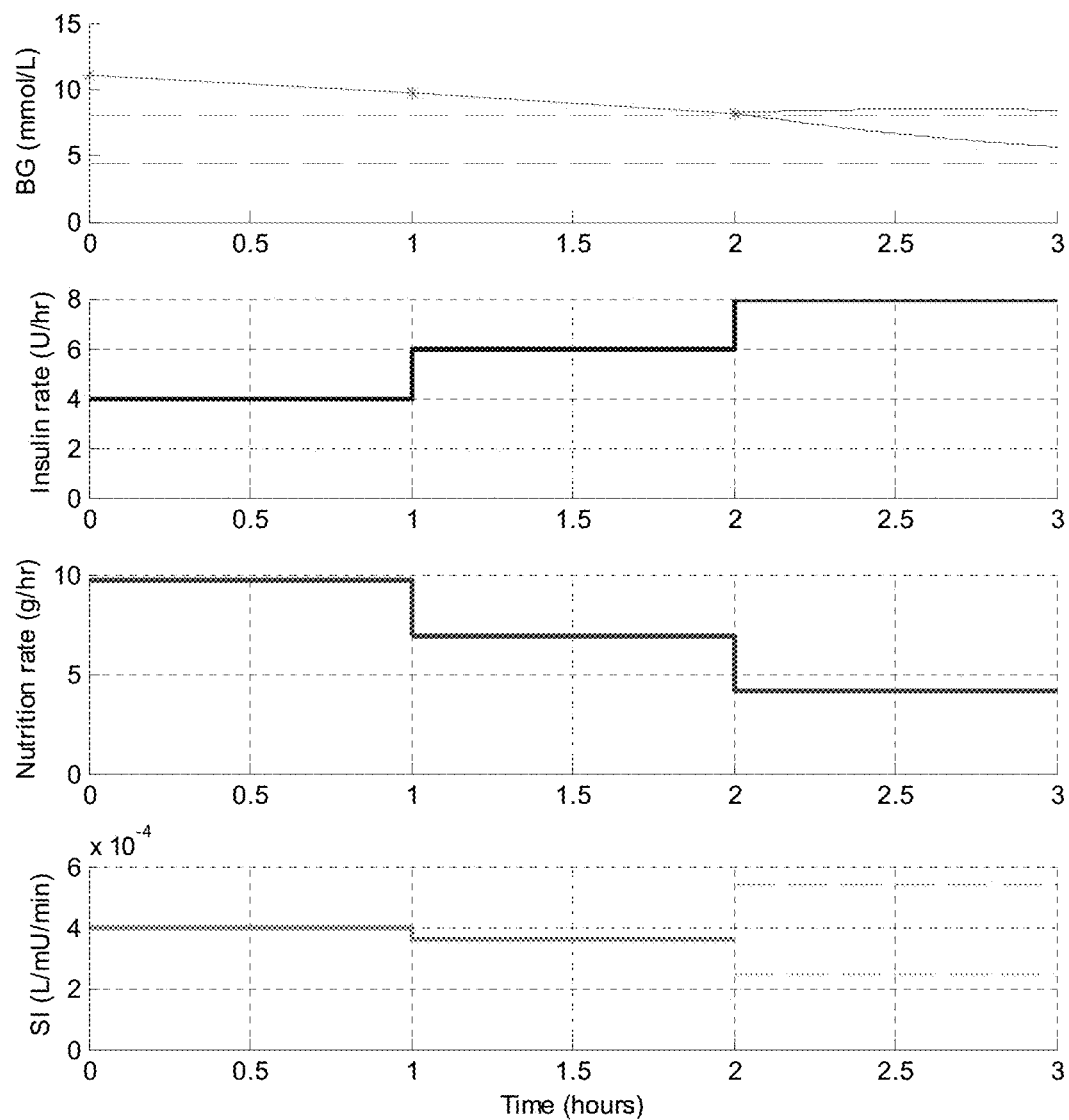
FIG. 6 shows the input values to calculate SI(t=3) in accordance with an embodiment of the present invention.
Figure 7:
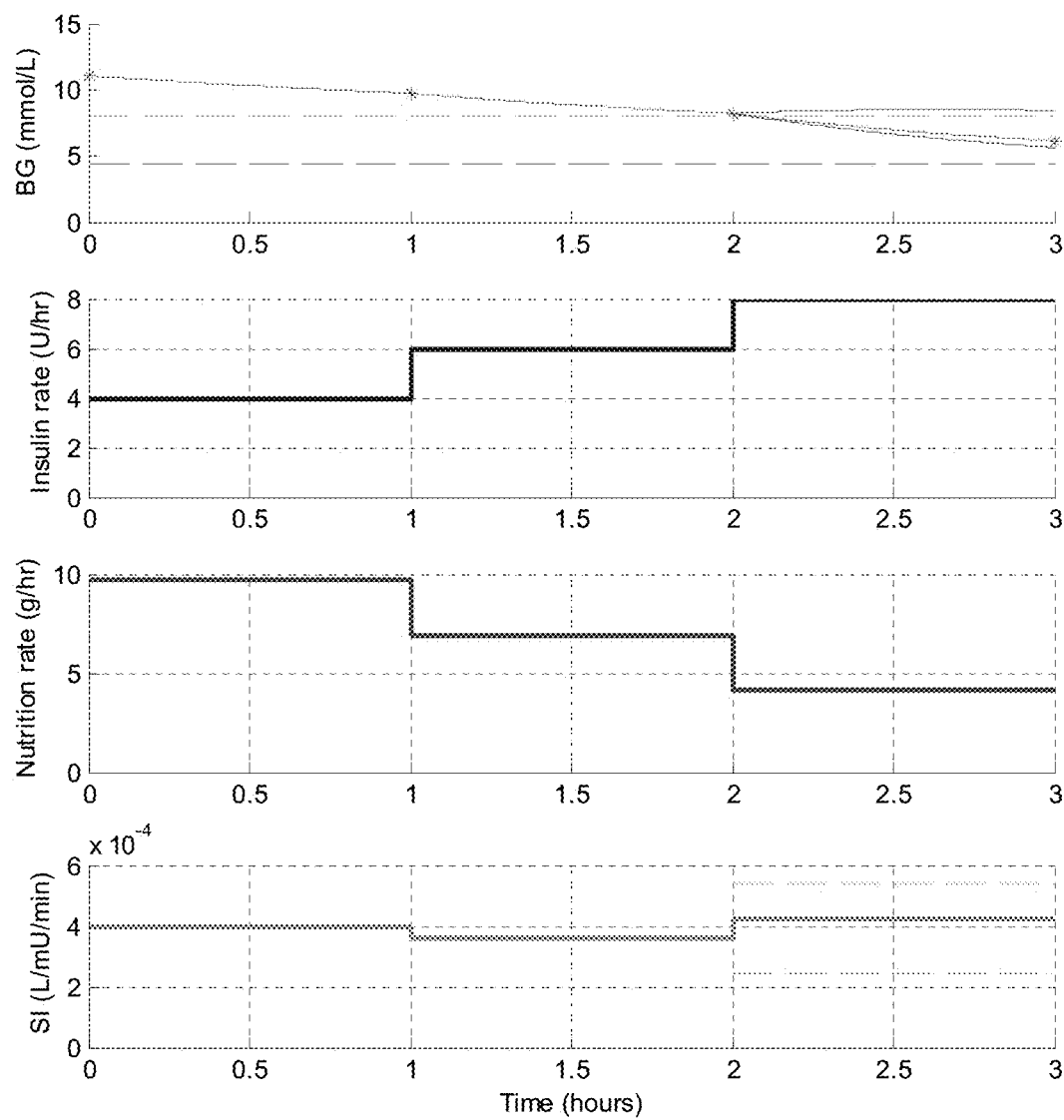
FIG. 7 shows the calculation of SI(t=3) using the physiological model in accordance with an embodiment of the present invention.

FIG. 5 shows prediction of BG traces ($5^{th}$ and $95^{th}$ percentiles given the $95^{th}$ and $5^{th}$ SI percentiles values) for different combination of insulin and nutrition inputs. The green line (no insulin and full nutrition) results in higher predicted BG, whereas the blue line (higher insulin and lower nutrition rates) results in lower predicted BG values. The blue option represented here is the one calculated by STAR (within the possible insulin/nutrition combinations according to ICU specifications).

This can be done for the 2 and 3 hours prediction.

Step 5 (Treatment selection):

Now that STAR calculated the best treatment it will suggest the determined combination to the nurse. STAR can offer 2 and/or 3 hourly treatments if and only if an existing solution met the safety criteria (and if not restricted by other constraints).

Nurses are thus able to choose between the 1-3 hourly treatment (if available), that seems best to match their clinical judgement.

In this case study, only the 1-hour treatment is possible (because current BG is outside the target range). The only suggested option by STAR thus corresponds to: 8 U/h of insulin (increase of 2 U/h) 4.1 g/h of nutrition (decrease of 30% of max cal. Intake) The new measured BG(t=3) is within the predicted band by STAR.

The new corresponding identified SI(t=3) value is within the predicted SI range.

Simulation Overview: The full simulation results are shown in FIG. 8, with the corresponding BG prediction range for each treatment selected.

Figure 8:
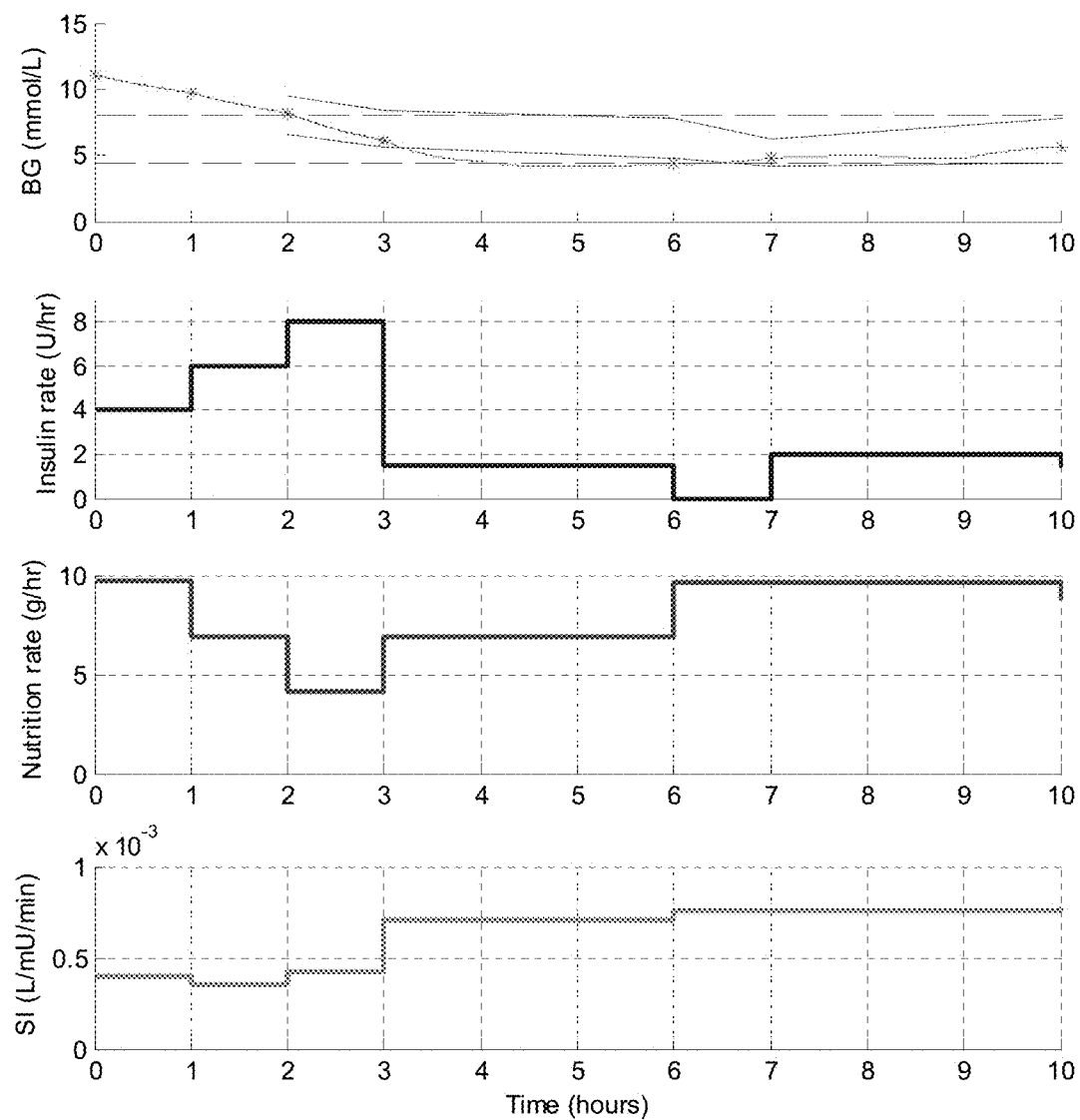
FIG. 8 shows BG in a desired range with inputs of insulin and nutrition over t=0 to t=10) in accordance with the Example of the present invention.

As shown in top panel of FIG. 8, at t=3, the 3-hour treatment was selected, and ended up slightly lower than predicted and very close to the lower limit of the safe target band. This explains the following 0 U/h of insulin and 100% nutrition input treatment suggestion. The predicted BG (blue line) will never be lower than the black dashed line unless treatment-independent (0 U/hr and full nutrition target).

Discussion of main results. Estimating changes in insulin sensitivity underpins the ability of STAR to respond in a patient-specific manner to potential future changes in patient glycaemic control requirements, resulting in safe and effective control strategies. If the distributions of forecast likely SI changes are narrower, then control can be further improved, with tighter control in more stable patients, and better avoidance of hypo-glycaemia in patients that exhibit high glycaemic variability.

The current invention is more patient-specific, and better predicts likely BG outcomes as compared to the prior model. These results translate into more aggressive insulin dosing where patients are more stable and SI outcomes are more certain, and less aggressive, lower insulin doses in patients who are more variable. Greater patient-specificity also reduces risk for more variable patients. The current invention leads to tighter and less variable control with greater safety from hypo-glycaemia, and thus improved outcomes.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed is:

1. A method for controlling the blood glucose level of a patient comprising the steps of:
   a) measuring a blood glucose level and determining an insulin sensitivity of the patient;
   b) measuring, subsequent to step a), the blood glucose level and determining the current insulin sensitivity of the patient;
   c) estimating with a multi-dimensional model, comprising delta SI, an adjustment needed to obtain a blood glucose level between a desired lower and upper confidence interval after administration of the adjustment to the patient;
   d) administering the adjustment to the patient; and
   e) repeating steps b) through d) until a desired state of health is achieved.

2. The method of claim 1, wherein the multi-dimensional model comprises clinical input data comprising current SI, prior SI, % delta SI, current blood glucose level and prior blood glucose level.

3. The method of claim 2, wherein the clinical input data is from an individual or group or sub-cohort of individuals.

4. The method of claim 2, wherein the multi-dimensional model provides a risk assessment based upon a given insulin or nutrition input.

5. The method of claim 4, wherein the assessment is of light, mild, moderate or severe hypoglycemia defined by specific blood glucose levels.

6. The method of claim 2, wherein a likelihood is assessed of any set of input data occurring given the number of points grouped within the same set of input data and the total number of input data point groups in the entire set of associations.

7. The method of claim 2, wherein the multi-dimensional model is used to assess for potential input errors in SI, the clinical data used to evaluate SI, and/or other input data when an input has very low probability of occurrence and thus lies in a region of low or no existing data.

8. The method of claim 1, wherein the adjustment comprises insulin administration, nutrition, exercise, or combinations thereof.

9. The method of claim 1, wherein the desired lower and upper confidence interval comprises 5% and 95% or 10% and 90%, respectively.

10. The method of claim 1, wherein the multi-dimensional model is based on the determined current insulin sensitivity and a % change in insulin sensitivity from a prior insulin sensitivity value, and the adjustment comprises an insulin/nutritional adjustment needed to obtain a blood glucose level between a desired lower and upper confidence interval after administration of the estimated insulin/nutritional adjustment to the patient.

11. A device for controlling the blood glucose levels of a patient, comprising:

a processor programmed to forecast with a multi-dimensional model based on a current insulin sensitivity and a % change in insulin sensitivity from a prior insulin sensitivity value, an adjustment needed to obtain a blood glucose level between a desired lower and upper confidence interval after administration of the adjustment to the patient;

a memory;

a data input; and a display.

12. The device of claim 11, wherein the processor is programmed to forecast with a multi-dimensional model based on the current insulin sensitivity and the % change in insulin sensitivity from a prior insulin sensitivity value, an insulin/nutritional adjustment needed to obtain a blood glucose level between the 5% and 95% confidence interval after administration of the insulin/nutritional adjustment to a patient.

\* \* \* \* \*